United States Patent [19]

Gauthier et al.

[11] Patent Number: 5,130,478

[45] Date of Patent: Jul. 14, 1992

[54] PROCESS FOR THE PREPARATION OF CHLORIDES OF CHLORINATED CARBOXYLIC ACIDS

[75] Inventors: Patricia P. Gauthier, Cerny; Michel M. Le Moult; Claude Rochelle, both of Toulouse; Jean-Pierre G. Senet, Herbeauvilliers-Buthiers, all of France

[73] Assignee: Societe Nationale de Poudres et Explosifs, Paris, France

[21] Appl. No.: 623,187

[22] Filed: Dec. 6, 1990

[30] Foreign Application Priority Data

Dec. 6, 1989 [FR] France ............... 89 16094

[51] Int. Cl.$^5$ .............................. C07C 51/09
[52] U.S. Cl. ............................................ 562/857
[58] Field of Search ................................. 562/857

[56] References Cited

U.S. PATENT DOCUMENTS 2,778,852 1/1957 Adam et al. ................... 562/857
4,764,310 8/1988 Buysch ......................... 562/857

FOREIGN PATENT DOCUMENTS 1080261 12/1954 France .
2227255 11/1974 France .
0253214 1/1988 France .

Primary Examiner—Paul J. Killos
Attorney, Agent, or Firm—Cushman, Darby & Cushman

[57] ABSTRACT

The invention relates to a process for the preparation of chlorides of chlorinated carboxylic acids of formula

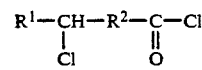

in which $R^2$ denotes the radical $(CH_2)_n$, n being an integer from 2 to 4, or the radical $-CH_2-C(C_6H_5)_2-$ and $R^1$ denotes a hydrogen atom or an alkyl radical containing from 1 to 4 carbon atoms, which consists in reacting the lactones of formula

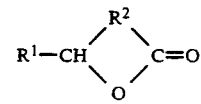

in which $R^1$ and $R^2$ have the above meanings, with phosgene at a temperature of 90° to 180° C., while employing as catalysts trisubstituted phosphine oxides or sulphides.

The process according to the invention makes it possible to obtain chlorides of chlorinated carboxylic acids of high purity which exhibit an excellent stability to light and to heat and which are very useful as synthesis intermediates.

9 Claims, No Drawings

PROCESS FOR THE PREPARATION OF CHLORIDES OF CHLORINATED CARBOXYLIC ACIDS

The invention relates to a process for the preparation of chlorides of chlorinated carboxylic acids. It relates more particularly to a process for the preparation of chlorides of chlorinated aliphatic carboxylic acids by phosgenation of aliphatic lactones.

Patent FR No. 1,080,261 describes the preparation of chlorides of chlorinated carboxylic acids by phosgenation of lactones, in particular of 4-butyrolactone in the presence of pyridine as a catalyst at a temperature of 120° C. However, it is difficult to reproduce the results cited, in particular those of Example 2, as shown in European Patent Application No. 253,214.

In the paper by D. J. Burton and W. M. Koppes (J. Org. Chem., vol. 40, No. 21, 1975, pp. 3026 to 3031), the aromatic ortho-chloromethylbenzoyl chloride has been obtained from the corresponding aromatic lactone with excess dichlorotriphenylphosphorane, but this compound is a very costly laboratory reactant which is not stable and which is particularly sensitive to hydrolysis. In addition, it reacts with the acid chloride formed, and it is preferable to employ it after it has been complexed with a Lewis acid such as $BF_3$, and this makes the process still more complicated. Apart from the conversion of the phthalide referred to, no other test has been carried out starting with other lactones.

According to recently filed European Patent Application EP No. 253,214, the phosgenation of lactones such as butyrolactone, valerolactone or caprolactone is carried out in the presence of a quaternary ammonium salt at elevated temperature, and preferably also in the presence of hydrochloric acid. However, the quaternary ammonium salts employed as catalysts present the disadvantage of being rather unstable at elevated temperature and consequently lose some of their activity. Hydrochloric acid employed in a large quantity is particularly corrosive at high temperature and requires special plants and precautions. Side reactions take place. The lactone polymerises and proper stirring of the mixture is not easy. Other impurities are formed by decomposition. The application of this process is consequently difficult. A number of successive operations are necessary to obtain good yields.

Chlorides of chlorinated carboxylic acids have been particularly investigated for a number of years as synthesis intermediates for the manufacture of medications and plant-protection products, and there is therefore a need to obtain them simply and economically and in good yields. These chlorides must also exhibit good stability to light and in storage.

It has now been found that it is possible to prepare chlorides of chlorinated carboxylic acids of formula

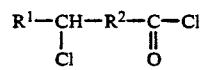 (I)

in which $R^2$ denotes the radical $(CH_2)_n$, being an integer from 2 to 4, or the radical $—CH_2-C(C_6H_5)_2—$ and $R^1$ denotes a hydrogen atom or an alkyl radical containing from 1 to 4 carbon atoms, by reaction of the lactones of formula

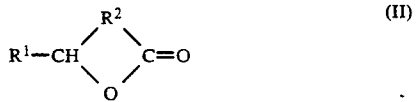 (II)

in which $R^1$ and $R^2$ have the above meanings, with phosgene at a temperature of between 90° and 180° C., while employing as catalysts trisubstituted phosphine oxides or sulphides of formula

 (III)

in which each of $Y^1$, $Y^2$ and $Y^3$, which are identical or different, denotes a linear or branched alkyl radical containing up to 18 carbon atoms or a phenyl radical which may carry one or more alkyl groups containing up to 4 carbon atoms and X denotes an oxygen atom or in which each of $Y^1$, $Y^2$ and $Y^3$, which are identical or different, denotes a phenyl radical which may carry one or more alkyl groups containing up to 4 carbon atoms and X denotes a sulphur atom, or the products of reaction of the compounds of formula III with chlorinating agents, or else mixtures of these compounds.

The lactones which can be converted according to the process according to the invention are preferably the lactones of formula II in which $R^1$ denotes a hydrogen atom or a methyl radical. By way of example there may be mentioned 4-butyrolactone, 4-valerolactone, 5-valerolactone, 6-caprolactone and 2,2-diphenyl-4-butyrolactone.

Catalysts which are suitable within the scope of the present invention are the compounds of formula III in which $Y^1$, $Y^2$ and $Y^3$, which are identical or different, denote a linear or branched alkyl radical containing up to 12 carbon atoms or a phenyl radical which may carry one or more methyl groups.

The compounds of formula III may also be replaced by products of their reaction with known chlorinating agents such as oxalyl chloride, thionyl chloride, phosgene and phosphorus pentachloride, which are obtained conventionally by mixing the compounds.

It is also possible to employ a mixture of the compounds of the formula III and of these reaction products.

As examples of catalysts which may be employed according to the invention there may be mentioned tributylphosphine oxide, trioctylphosphine oxide, tridodecylphosphine oxide, triphenylphosphine oxide and triphenylphosphine sulphide and tri-p-tolylphosphine oxide.

The preferred catalyst within the scope of the present invention are trioctylphosphine oxide and triphenylphosphine oxide.

Very small quantities of the catalysts described above are sufficient for good implementation of the process. They are generally between 0.1 and 5 mol% relative to the starting lactone, and preferably between 0.5 and 2.5%.

The reaction temperature may be between 90° and 180° C. It is preferably between 120° and 160° C.

The reaction is preferably carried out in the absence of solvent. However, a solvent medium which is inert towards the compounds present in the mixture, in particular phosgene, may be added. Solvents which may be mentioned are, for example, chlorinated or unchlorinated aromatic solvents whose boiling point is sufficiently high, such as monochlorobenzene, dichlorobenzene, isopropylbenzene and xylenes.

The phosgene is generally added in stoichiometric quantity or in excess. This excess is preferably between 10 and 20%.

The process according to the present invention may be carried out either discontinuously or continuously at atmospheric pressure or at a pressure close to atmospheric pressure in known phosgenation devices.

According to a suitable operating procedure, the lactone, the catalyst and optionally the solvent are first of all introduced into the reactor. The reaction mixture is heated to the chosen temperature and gaseous phosgene is then progressively passed through the mixture. The carbon dioxide formed and the excess phosgene are cooled in a condenser. At the end of the reaction the mixture is cooled and a stream of nitrogen is passed through. The chlorinated acid chloride formed may be isolated in conventional manner, for example by distillation or by crystallisation.

The process according to the invention makes it possible, by starting with commercially available raw materials, to obtain high yields of chlorides of chlorinated carboxylic acids of high purity, which additionally exhibit an excellent stability to light and to heat.

The phosphine oxides employed as catalysts are highly stable under the conditions of the present reaction and may be employed one or more times with the same efficiency. They can therefore be recycled or the distillation residue may be reemployed for a new operation.

The chlorides of chlorinated carboxylic acids which are obtained are particularly useful as synthesis intermediates, for example for the preparation of chlorinated ketones or for forming pharmaceutical products such as neuroleptics, antiallergens, antidepressants and antidiarrhoeals, or plant-protection products such as insecticides.

The following examples illustrate the invention:

EXAMPLE 1

172 g (2 moles) of 4-butyrolactone and 5.6 g (0.02 moles) of triphenylphosphine oxide are introduced into a phosgenation reactor comprising a thermometer, a stirrer, a gas delivery and a condenser. The mixture is heated to 140° C. and gaseous phosgene is bubbled through.

After 240 g of phosgene have been introduced over 9 h of reaction time, the reaction mixture is cooled and degassed by bubbling with nitrogen. A distillation at reduced pressure makes it possible to recover 233.5 g of 4-chlorobutyryl chloride, that is an 82% yield (boiling point: 82° C. at 33 mm Hg). The purity of this chloride, determined by GPC analysis, is 99%.

Example 2

2,500 g (29 moles) of 4-butyrolactone and 80 g (0.285 moles) of triphenylphosphine oxide are introduced into a 4-l reactor fitted with the same devices as previously. The mixture is heated to 140° C. and gaseous phosgene is introduced slowly. The conversion is complete after 12 h, after 3,200 g of phosgene (32.3 moles) have been introduced.

After degassing and distillation at reduced pressure, 3,560 g of 4-chlorobutyryl chloride are obtained, whose purity, determined by GPC analysis, is 99%, that is an 86% yield (boiling point 70° C. at 20 mm Hg).

EXAMPLE 3

Into a 4-l reactor of the same type as that of Example 2 are introduced 2,500 g (29 moles) of 4-butyrolactone, 500 g of the reactor residue from the operation described in Example 2, containing the equivalent of 80 g (0.285 moles) of triphenylphosphine oxide. The mixture is heated to 140° C. and gaseous phosgene is introduced slowly. The conversion is complete after 13 h, after 3,400 g of phosgene (34.34 moles) have been introduced. After degassing and distillation at reduced pressure 3,640 g of 4-chlorobutyryl chloride (25.8 moles) of 98.9% purity (GPC analysis) are obtained, that is an 88.9% yield (boiling point: 70° C. at 20 mm Hg).

The results of the tests of stability of the chloride obtained to light and in a climatic chamber are as follows:

| Stability to light | APHA colour |
| --- | --- |
| Temperature: 20° C. | Initial: 30 |
| Period: 1 month | Final: 30 |
| Stability in a climatic chamber | APHA colour |
| Temperature: 50° C. | Initial: 30 |
| Period: 1 month | Final: 30 |

EXMAPLE 4

As in Example 1, 172 g (2 moles) of 4-butyrolactone and 7.7 g (0.02 moles) of trioctylphosphine oxide are introduced into the reactor. The mixture is heated to 150° C. and 272 g of gaseous phosgene are introduced over 15 h. The reaction mixture is cooled and degassed. A distillation at reduced pressure makes it possible to recover 218.6 g of 4-chlorobutyryl chloride, 98% pure (GPC analysis), that is a 76% yield (boiling point 60° C. at 14 mm Hg).

EXAMPLE 5

As in Example 1, 200 g (2 moles) of 4-valerolactone and 11.2 g (0.04 moles) of triphenylphosphine oxide are introduced into the reactor. The mixture is heated to 150° C. and 268 g of gaseous phosgene are introduced over 9 h. The reaction mixture is cooled and degassed. 4-chloromethylbutyryl chloride is separated off by distillation (boiling point: 68° C. at 18 mm Hg). The yield is 70% based on the 4-valerolactone which has reacted.

EXAMPLE 6

As in the preceding example, 200 g (2 moles) of 5-valerolactone and 11.2 g (0.04 moles) of triphenylphosphine oxide are introduced into the reactor. The mixture is heated to 140° C. After 236 g of gaseous phosgene have been introduced over 5 h the reaction mixture is cooled and degassed. A distillation at reduced pressure makes it possible to recover 217 g of 5-chlorovaleryl chloride with a purity of 99% (GPC analysis), that is a 70% yield (boiling point: 59° C. at 0.25 mm Hg).

EXAMPLE 7

As previously, 228.4 g (2 moles) of 6-caprolactone and 5.6 g (0.02 moles) of triphenylphosphine oxide are introduced into the reactor. The mixture is heated to 140° C. and 265 g of gaseous phosgene are introduced gradually. The conversion of the lactone is complete after 6 h. A distillation at reduced pressure makes it possible to isolate 270 g of 6-chlorocaproyl chloride with a purity of 99%, that is a 79% yield (boiling point: 67° C. at 0.3 mm Hg).

EXAMPLE 8

As previously, 100 g (0.419 moles) of 2,2-diphenyl-4-butyrolactone and 1.15 g ($4 \times 10^{-3}$ moles) of triphenylphosphine oxide are introduced into the reactor. The mixture is heated gradually to 150° C. and 72 g of gaseous phosgene are introduced slowly at this temperature. After 15 h of reaction the degree of progress of the reaction is 60%. The mixture is then cooled and then degassed with nitrogen. 2,2-Diphenyl-4-chlorobutyryl chloride is obtained by distillation. Boiling point 200° C. at 0.9 mm Hg.

EXAMPLE 9

172 g (2 moles) of 4-butyrolactone and 5.9 g (0.02 moles) o triphenylphosphine sulphide are introduced into a phosgenation reactor comprising a thermometer, a stirrer, a gas delivery and a condenser. The mixture is heated to 140° C. and gaseous phosgene is bubbled through. After 273 g of phosgene have been introduced over 8 h of reaction time the reaction mixture is cooled and degassed by bubbling with nitrogen. A distillation at reduced pressure makes it possible to recover 200 g of 4-chlorobutyryl chloride (99% purity by GPC analysis), that is a 70% yield.

EXAMPLE 10

172 g (2 moles) of 4-butyrolactone and 4.4 g (0.02 moles) of tributylphosphine oxide are introduced into the reactor in the same way as in the preceding example. The temperature is raised to 150° C. and gaseous phosgene is bubbled through. After 280 G of phosgene have been introduced over 15 hours' reaction, the reaction mixture is cooled and degassed by bubbling with nitrogen. After distillation at reduced pressure 171 g of 4-chlorobutyryl chloride are collected (99% purity by GPC analysis), that is a 60% yield.

We claim:

1. Process for the preparation of chlorides of chlorinated carboxylic acids of formula

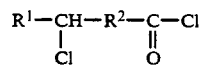 (I)

in which $R^2$ denotes the radical $(CH_2)_n$, n being an integer from 2 to 4, or the radical $-CH_2-C(C_6H_5)_2-$ and $R^1$ denotes a hydrogen atom or an alkyl radical containing from 1 to 4 carbon atoms, by reaction of the lactones of formula

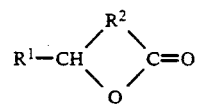 (II)

in which $R^1$ and $R^2$ have the above meanings, with phosgene, characterised in that the reaction is carried out at a temperature of 90° to 180° C. while employing as catalysts trisubstituted phosphine oxides or sulphides of formula
in which each of $Y^1$, $Y^2$ and $Y^3$, which are identical or different, denotes a linear or branched alkyl radical containing up to 18 carbon atoms or a phenyl radical which may carry one or more alkyl groups containing up to 4 carbon atoms and X denotes an oxygen atom or in which each of $Y^1$, $Y^2$ and $Y^3$, which are identical or different, denotes a phenyl radical which may carry one or more alkyl groups containing up to 4 carbon atoms and X denotes a sulphur atom, or the products of reaction of compounds of formula III with chlorinating agents, or else mixtures of these compounds.

2. Process according to claim 1, characterised in that the catalyst is added in proportions of between 0.1 and 5%, preferably between 0.5 and 2.5 mol% relative to the lactone.

3. Process according to claim 1 or 2, characterised in that each of $Y^1$, $Y^2$ and $Y^3$, which are identical or different, denotes a linear or branched alkyl radical containing up to 12 carbon atoms or a phenyl radical which may carry one or more methyl groups.

4. Process according to claim 1 or 2, characterised in that phosgene is added in stoichiometric quantity or in excess, preferably between 10 and 20 mol% relative to the lactone.

5. Process according to any one of the preceding claim 1 or 2, characterised in that the catalyst employed is trioctylphosphine oxide or triphenylphosphine oxide.

6. Process according to claim 1 or 2, characterised in that the temperature is between 120° and 160° C.

7. Process according to claim 1 or 2, characterised in that the reaction takes place in a solvent medium which is inert towards the compounds present, chosen from chlorinated or unchlorinated aromatic hydrocarbons.

8. Process according to claim 1 or 2, characterised in that $R^1$ denotes a hydrogen atom or a methyl radical.

9. Process according to claim 1 or 2, characterised in that the lactone is chosen from 4-butyrolactone, 4-valerolactone, 5-valerolactone, 6-caprolactone and 2,2-diphenyl-4-butyrolactone.

* * * * *

UNITED STATES PATENT AND TRADEMARK OFFICE
CERTIFICATE OF CORRECTION

PATENT NO. : 5,130,478
DATED : July 14, 1992
INVENTOR(S) : Patricia P. Gauthier et al.

It is certified that error appears in the above-identified patent and that said Letters Patent is hereby corrected as shown below:

Col. 1, line 64, "being" should read -- n being --.

Col. 5, line 39, "280 G" should read -- 280 g --.

Col. 6, line 14, after "formula" insert $$-- \begin{array}{c} Y^1 \\ Y^2 - \\ Y^3 \end{array} \!\!\! \diagdown \!\!\! \diagup \; P=X \quad (III) \quad --$$

Signed and Sealed this

Twenty-eighth Day of September, 1993

Attest:

BRUCE LEHMAN

Attesting Officer  Commissioner of Patents and Trademarks